(12) United States Patent
Cline et al.

(10) Patent No.: US 8,100,875 B2
(45) Date of Patent: Jan. 24, 2012

(54) OSTOMY COUPLING

(75) Inventors: John Cline, New Brunswick, NJ (US);
John L. Blum, Toms River, NJ (US);
Gary Stacey, Cambridgeshire (GB);
Phillip Davies, West Midlands (GB);
Trevor Beckett, Cambridgeshire (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 678 days.

(21) Appl. No.: 11/548,553

(22) Filed: Oct. 11, 2006

(65) Prior Publication Data
US 2007/0088300 A1    Apr. 19, 2007

Related U.S. Application Data

(60) Provisional application No. 60/725,539, filed on Oct. 11, 2005.

(51) Int. Cl.
*A61F 5/44* (2006.01)
(52) U.S. Cl. ........ 604/328; 604/110; 604/111; 604/327; 604/332; 604/333; 604/334; 604/335; 604/336; 604/337; 604/338; 604/339; 604/340; 604/341; 604/342; 53/133.6; 53/133.7; 53/133.8
(58) Field of Classification Search .......... 604/327–328, 604/110–111, 332–342; 53/133.6, 133.7, 53/133.8
See application file for complete search history.

(56) References Cited

U.S. PATENT DOCUMENTS

| | | | | |
|---|---|---|---|---|
| 3,142,280 A * | 7/1964 | Heinle | .............................. | 413/12 |
| 3,379,155 A * | 4/1968 | Wheaton et al. | ................ | 413/17 |
| 3,380,609 A * | 4/1968 | Potts | .............................. | 215/254 |
| 3,589,543 A * | 6/1971 | Weigand | ........................ | 215/213 |
| 3,921,366 A * | 11/1975 | Coop | ............................... | 53/420 |
| 4,427,128 A * | 1/1984 | Heyn | ............................ | 220/270 |
| 4,456,139 A * | 6/1984 | Kent | ............................. | 215/252 |
| 4,467,933 A * | 8/1984 | Wilkinson et al. | ............. | 220/623 |
| 4,526,283 A * | 7/1985 | Skinner | ........................ | 215/256 |
| 4,784,282 A * | 11/1988 | Le Bret et al. | ................ | 220/619 |
| 4,893,452 A * | 1/1990 | Bruce et al. | ..................... | 53/420 |
| 4,950,223 A * | 8/1990 | Silvanov | ......................... | 600/32 |
| 5,292,018 A * | 3/1994 | Travisano | ...................... | 215/246 |
| 5,312,381 A | 5/1994 | Brooks | | |
| 6,023,834 A * | 2/2000 | Brown et al. | .................... | 29/509 |
| 6,723,079 B2 * | 4/2004 | Cline | ............................ | 604/337 |
| 2004/0193122 A1 * | 9/2004 | Cline et al. | ..................... | 604/332 |

FOREIGN PATENT DOCUMENTS

| | | | |
|---|---|---|---|
| EP | 415520 | * | 3/1991 |
| GB | 2261376 | | 5/1993 |
| GB | 2306889 | | 5/1997 |
| GB | 2368528 | | 5/2002 |

* cited by examiner

*Primary Examiner* — Tatyana Zalukaeva
*Assistant Examiner* — Ginger T Chapman
(74) *Attorney, Agent, or Firm* — Stuart E. Krieger

(57) ABSTRACT

A single-use ostomy appliance is described including an ostomy coupling for releasable coupling first and second portions at a stomal orifice. The two portions may be separable body-side and non-body-side parts, or the two portions may be portions of a unitary ostomy device such as a controlled evacuation device. The coupling includes a mechanical fastener configured such that the coupling is rendered substantially not resecurable after the fastener is released.

4 Claims, 12 Drawing Sheets

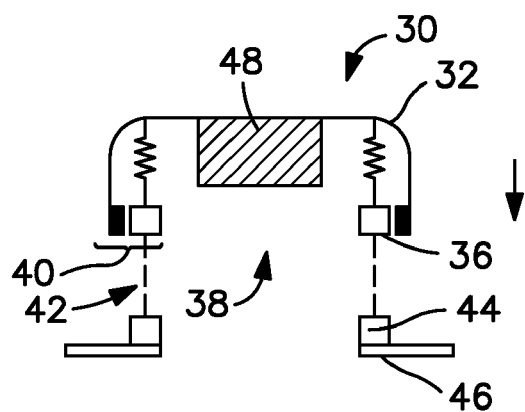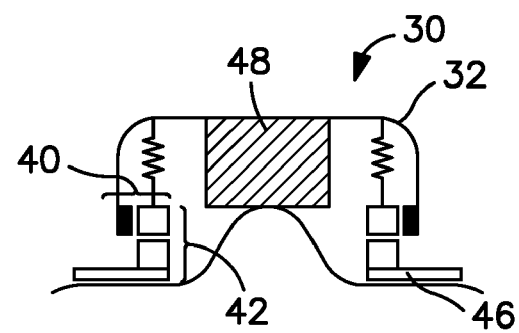
FIG. 3  FIG. 4

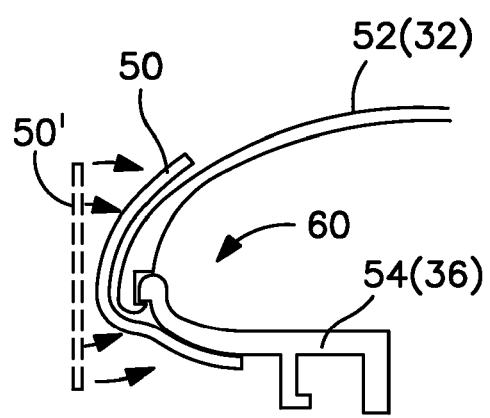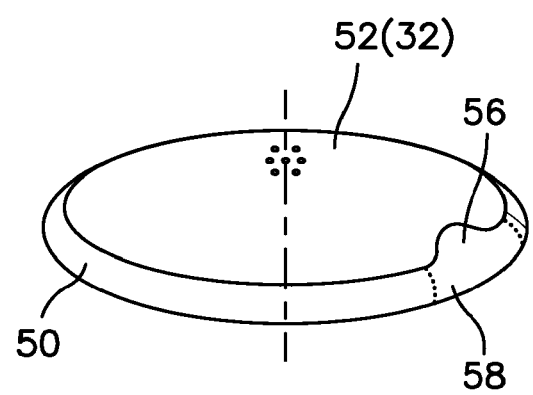
FIG. 7  FIG. 8

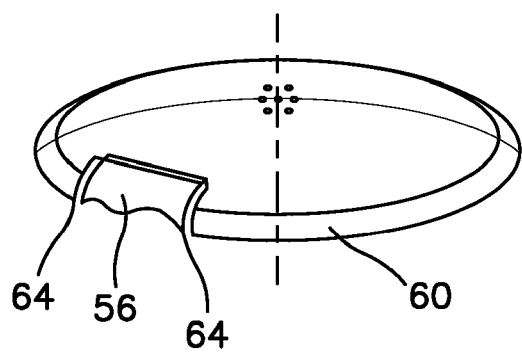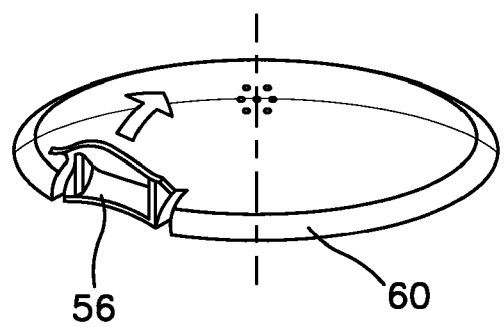
FIG. 15  FIG. 16

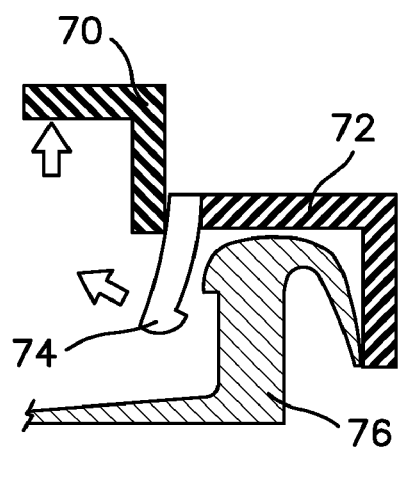
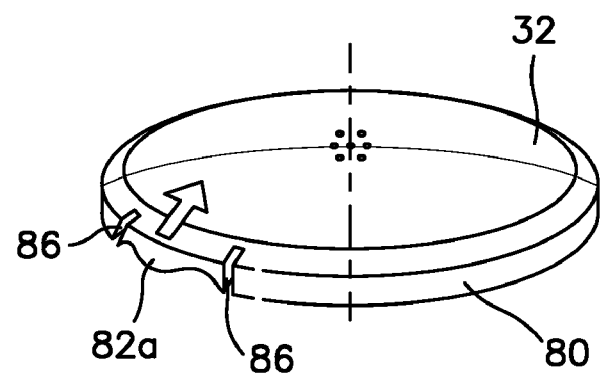
FIG. 19  FIG. 20

OSTOMY COUPLING

FIELD OF THE INVENTION

The present invention relates to the field of ostomy couplings. It more particularly relates to releasably securing together a body-side coupling element and an appliance-side coupling element of an ostomy appliance at or around a stomal orifice. The ostomy appliance may include for example, a collection pouch, a stoma port (or plug or cap), or a controlled evacuation device.

BACKGROUND TO THE INVENTION

The majority of conventional ostomy couplings are either of the mechanical fastening type, or the adhesive fastening type. A mechanical interference fastening type may be especially suitable where the advantage of a secure and positive mechanical fastening is desired.

Conventional ostomy couplings using a mechanical interference fastening generally comprise at least two coupling elements, one of which may, for example, be a body-side coupling element for adhesive attachment to the body. The other coupling element may, for example, be a non-body-side coupling element (also referred to as an appliance-side element), for example, a bag-side coupling element integrated with a collection pouch. The two coupling elements carry co-operating fasteners to allow the coupling elements to be repeatedly attached and separated, whereby the operative part of the appliance may be releasably attached and detached with respect to the body. Such an arrangement permits the body-side member to be worn on the body for a relatively long length of time, and permits frequent removal or changes of the operative part of the appliance without having to remove the body-side element. The conventional approach to designing such ostomy couplings has focused on enhancing the ease and convenience with which the ostomy coupling elements may be repeatedly attached and separated with respect to each other.

SUMMARY OF THE INVENTION

In contrast to the above, one aspect of the present invention provides an ostomy coupling using a releasable mechanical interference fastener that is configured to provide secure mechanical fastening attachment between the coupling members only once. For example, the fastener is rendered substantially inoperative after the first time that the fastener is released.

Such an arrangement may be especially suitable for an ostomy appliance in the form of, or comprising, a disposable unit intended to be disposed of after it has been used once. The term ostomy includes, but is not limited to, any of colostomy, ileostomy and urostomy. There are many reasons why a particular disposable unit may be intended not to be re-usable. Such reasons include hygiene if, for example, a disposable unit is of a type that is not easily emptied and/or is not easily cleaned. Certain disposable ostomy appliance units with a collection chamber without a drainage outlet, and/or a collection chamber that includes tight folds, may be difficult to empty or clean, or may be difficult to re-form into an original operative shape. Other disposable ostomy appliance units may simply not be designed to be used more than once, whether for hygiene reasons, or other reasons. For example, certain types of controlled evacuation devices or stoma ports, plugs or caps may include a seal that makes intimate contact with the sensitive stomal tissue to seal the stoma closed. It may be inadvisable to try to re-use the device after a first time that the device is removed, for example, if the seal may be contaminated by stomal discharge. Other examples may be disposable ostomy appliance units that are designed to withstand reliably only a single anticipated use. For example, the disposable unit may use lightweight or inexpensive materials or joins, or may use materials or joins that are intended to deteriorate over time (such as materials specifically intended to be quickly biodegradable, or to be destructible when flushed in a toilet). The above is merely a non-exhaustive list illustrating many important applications of the present invention.

Thus, the present invention can provide the advantages of a secure mechanical fastening, yet, the invention can obstruct re-use of a disposable ostomy appliance unit that is intended only for single use. The invention may be applied to any ostomy coupling comprising first and second coupling elements for releasably fastening two portions of an ostomy appliance together at, or around, a stomal orifice. After the two coupling elements have been separated, for example, as part of the use of the appliance, the invention may obstruct re-fastening of the coupling elements, and thus obstruct re-use of the disposable unit.

In one form, the ostomy appliance comprises a body-side mounting unit to be worn on the body, and a disposable ostomy appliance unit attachable thereto. The body-side unit is intended for use more than once, whereas the disposable unit is intended for only single use. One of the coupling elements is carried by the body-side unit, and the other coupling element is carried by the disposable unit. The invention is used to prevent the appliance-side coupling element from being re-fastened securely to the body-side coupling element after first use, thereby to prevent re-use of the disposable unit. Configuring the coupling element of the appliance side to be rendered inoperative still permits the body-side coupling element to be used with a replacement disposable unit, without having to changing the body-side coupling element worn on the body.

In another form, the first and second portions are respective portions of the same disposable ostomy appliance unit. The disposable unit has two operative states, a first in which the first and second portions are fastened together, and a second in which the first and second portions are released. The invention is used to prevent refastening of the first and second portions of the disposable unit securely to each other after the first time the portions are released, thereby to obstruct re-use of the disposable unit.

At least one of the first and second coupling elements includes a stomal orifice intended to fit around a stoma. One of the first and second coupling elements is intended to support the other element at, or around, the stomal orifice. The releasable mechanical fastening between the coupling elements may be distributed between multiple positions around the stomal orifice and/or extend at least partly around the stomal orifice.

The releasable mechanical fastening includes at least one fastening portion, or bracing portion, or support portion, that is, in use, deformed or broken as part of an operation to separate the coupling elements the first time. The deformation or breakage provides a means by which one of the coupling elements is rendered unsuitable for re-fastening securely to the other coupling element.

In a closely related aspect, the present invention provides an ostomy coupling element having a mechanical fastening device that is configured such that the fastening device becomes substantially inoperative after the first time that the fastening device is disengaged to separate the coupling members. The coupling member may be integrated within an ostomy appliance. The coupling member may be an appliance-side coupling member.

In a further closely related aspect, the present invention may provide an ostomy appliance comprising first and second portions, each having a respective ostomy coupling element for mutual, releasable mechanical fastening to each other. The first portion could be an entrance portion of the appliance. The second portion could be an operative portion of the appliance. A collapsible/extendable collection chamber is provided between the first and second portions. At least the first coupling element has a stomal orifice therein. In use, one coupling element supports the other coupling element via the releasable mechanical fastening. The appliance would be configured to obstruct secure re-fastening of the first and second portions via the coupling elements after the first time that the mechanical fastening has been released. One or both of the coupling elements may be configured with a fastener that becomes substantially inoperative after the first time that the fastener is disengaged from the other coupling element.

The above aspects of the invention may be used in isolation or any two or more of the aspects may be used in combination.

BRIEF DESCRIPTION OF THE DRAWINGS

FIG. 3 is a schematic drawing of the second embodiment of the present invention showing a body side mounting unit and a controlled discharge device apart.

FIG. 4 is a schematic drawing of the second embodiment of FIG. 3 showing the body side mounting unit and the controlled discharge unit together.

FIG. 7 is a schematic drawing of part of a mechanical interference fastener.

FIG. 8 is a further schematic drawing of the mechanical interference fastener of FIG. 7 showing the tab for tearing and lines of perforation.

FIG. 15 is a schematic drawing of the second embodiment of the mechanical fastener of FIG. 11 with the tab for separation closed.

FIG. 16 is a schematic drawing of the second embodiment of the mechanical fastener of FIG. 11 with the tab for separation being lifted.

FIG. 19 is a schematic drawing showing a third embodiment of a mechanical fastener being disengaged from a coupling.

FIG. 20 is a schematic drawing showing a fourth embodiment of a mechanical fastener.

DETAILED DESCRIPTION OF THE INVENTION

Figure 1:
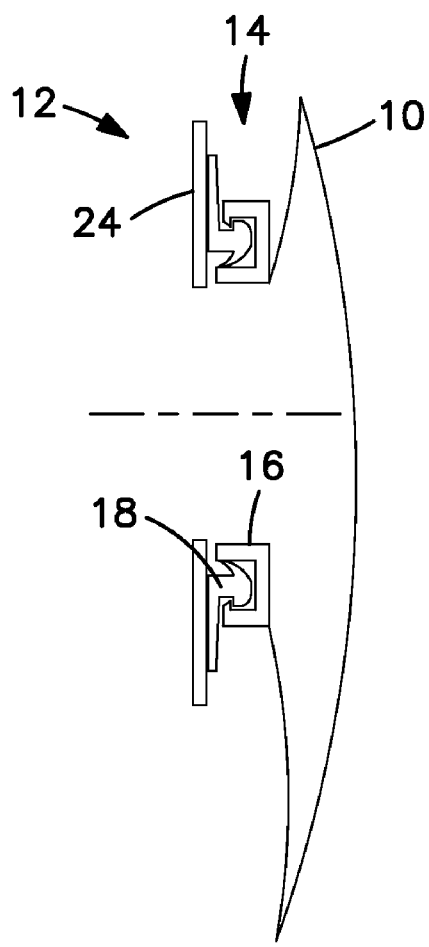
FIG. 1 is a schematic drawing of the first embodiment of the present invention showing the body side mounting unit and collection pouch together.
Figure 2:
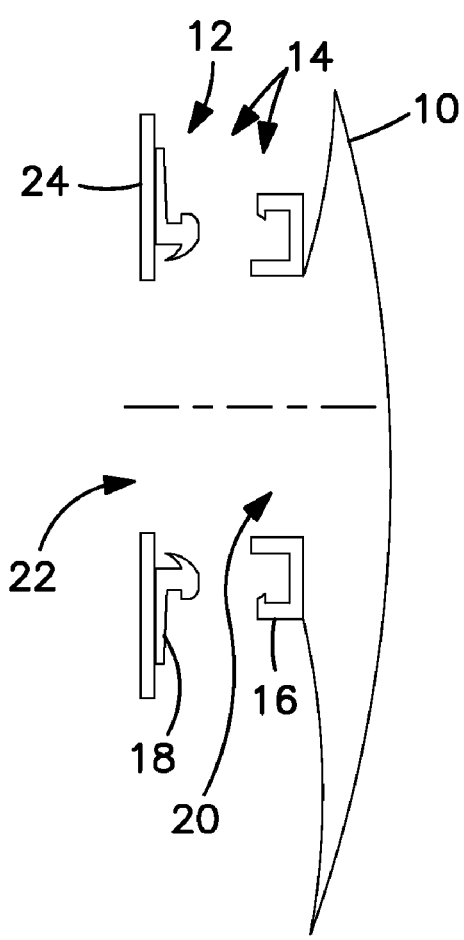
FIG. 2 is a schematic drawing of the first embodiment of FIG. 1 showing the body side mounting unit and collection pouch apart.

Referring to FIGS. 1 and 2, a first embodiment of an ostomy appliance comprises a disposable unit in the form of a collection pouch 10, and a re-usable unit in the form of a body-side mounting unit 12. The collection pouch 10 may be of a type that is intended for use only once, after which the pouch 10 is intended for disposal. The body-side mounting unit 12 is intended to remain on the body, and be used multiple times to permit replacement pouches 10 to be fitted and removed without having to remove the body-side mounting unit 12 from the body.

The collection pouch 10 is releasably fastened to the body-side mounting unit 12 by means of an ostomy coupling 14. The ostomy coupling 14 includes confronting first and second coupling members 16 and 18. The first ("non-body-side" or "pouch-side") coupling member 16 includes a first stomal orifice 20, and is carried by the pouch 10 at a pouch entrance aperture. The second ("body-side") coupling member 18 includes a second stomal orifice 22, and is carried by the body-side mounting unit 12 around a stomal aperture through the body-side mounting unit. The body-side mounting member 12 may have an adhesive backing 24 for adhesive attachment to a wearer's body.

The coupling members 16 and 18 include respective fastener parts for releasably securing the two coupling members 16 and 18 together by a mechanical interference fastening. Examples of suitable fastener parts are described later in more detail. The coupling members 16 and 18 are configured to permit the coupling members to be brought into mutual fastening engagement a first time (as illustrated in FIG. 1), for example, via a snap fit. The coupling members 16 and 18 are configured such that, when the coupling members 16 and 18 are disconnected in order to remove the pouch 10 when the pouch is full, the fastener part of, for example, the bag-side coupling member 18 becomes substantially inoperative. For example, the act of releasing the fastening the first time deforms (e.g., permanently) or break or weaken the fastener part or a brace or support therefor to render the fastener part substantially inoperative.

Thus the pouch 10 is intentionally be rendered incapable of being re-attached to the body-side mounting member 12 for re-use. The body-side mounting member 12 remains unaffected, allowing other pouches 10 (or other appliances) to be changed in place of the used pouch 10. The body-side coupling member 18 thus is configured for use for fastening attachment a plurality of times, whereas the bag-side coupling member 16 is configured for fastening attachment to the body-side coupling member 18 only once.

Referring to FIGS. 3-6, in a second embodiment, an ostomy appliance comprises a controlled discharge device 30. The controlled discharge device generally comprises a cap 32, a collection chamber in the form of a tube 34, and mounting ring 36. The tube 34 is collapsible, for example, in a bellows-like form. The mounting ring 36 comprises a stomal aperture 38. The cap 32, tube 34 and the mounting ring 36 are integrally molded or otherwise permanently joined to each other to form a unitary item.

The device 30 comprises two ostomy couplings 40 and 42. The first coupling 40 is formed between the cap 32 (acting as a first coupling member) and the mounting ring 36 (acting as a second coupling member). The first coupling 40 serves to fasten the cap 32 to the mounting ring 36 in an initial state of the device 30, as shown in FIG. 3. In the initial state, the tube 34 is collapsed substantially to a flat bellows form, and the cap 32 is held directly adjacent the mounting ring 36 and supported by the mounting ring 36. The second coupling 42 is formed between the mounting ring 36 (second coupling member) and a body-side coupling member 44 (acting as a third coupling member) of a body-side mounting member 46. The body-side mounting member 46 is similar to (or even the same as) the body-side mounting member 12 of the first embodiment.

The device 30 initially is supplied with the first coupling 40 already assembled, as shown in FIG. 3. The body-side mounting member 46 is supplied as a separate device not pre-assembled to the unit 39. The body-side mounting member 46 may already be worn on the body. Referring to FIG. 4, to use the device 30, the user fastens the device to the body-side mounting member 46 by means of the second ostomy coupling 42. The device 30 functions to prevent discharge from the wearer's stoma. A seal 48 is provided in the cap 32 to seal against the stomal tissue. The seal 48 functions in a similar way to that described in U.S. Pat. No. 6,723,079, the contents of which are incorporated herein by reference.

Figure 5:
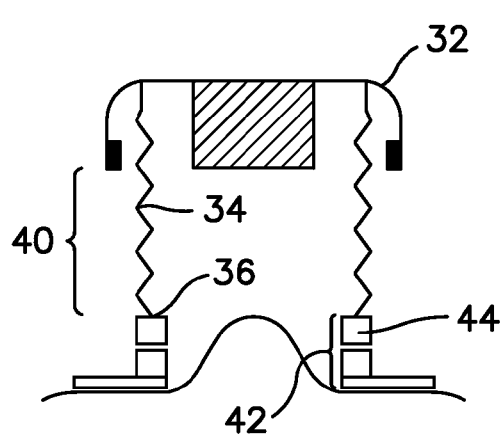
FIG. 5 is a schematic drawing of the second embodiment of FIG. 3 showing the controlled discharge device having an extended collection tube.
Figure 6:
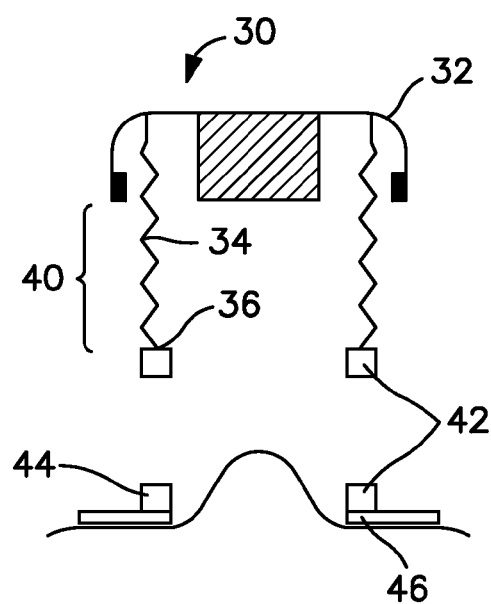
FIG. 6 is a schematic drawing of the second embodiment of FIG. 3 showing the body side mounting unit and controlled discharge device with an extended collection tube apart.

Referring to FIG. 5, when the user desires to allow a stomal discharge, the user releases the first coupling 40 to allow the cap 32 to be displaced away from the mounting ring 36. With the cap 36 (and optional seal 48) moved clear of the stoma, stomal discharge enters the tube 34. The tube 34 is extended as the cap 32 is displaced, to provide adequate room to collect the stomal discharge. Once the discharge has been collected, the device 30 is removed from the body-side mounting member 46 by releasing the second ostomy coupling 42 (FIG. 6).

One or both of the couplings 40 and 42 are configured not to be re-fastenable after the respective coupling 40 or 42 has been released the first time. Such a configuration of the coupling(s) prevents the device 30 from being used more than once. The device 30 is designed to be used only once, and disposed of thereafter. The device 30, in use, makes intimate contact with the stomal tissue, and so the advisability of re-use depends on the actual design of the device 30. For example, re-use might be inadvisable if, for example, the device 30 might be difficult to clean making re-use unhygienic, or if the tube 34 might be difficult to re-collapse to its original tight, flat bellows form, or if the seal 48 might not be as effective with repeated use.

For example, the first coupling 40 may be configured not to be re-fastenable after the first time the first coupling 40 is disconnected. A fastener part of, or between, the cap 32 and/or the mounting ring 32 is configured to become substantially inoperative after the first time the first coupling 40 is disconnected. Such a first coupling 40 prevents the device 30 from being re-used, by preventing the cap 30 from being re-coupled in an operative state to the mounting ring 36.

Additionally or alternatively, the second coupling 42 may be configured not to be re-fastenable, in a similar manner to the first embodiment. A fastener part of the mounting ring 36 for coupling to the body-side mounting member 44 is configured to become substantially inoperative after the first time the mounting ring 36 is detached from the body-side coupling member 44. Such a second coupling 42 prevents the device 30 from being re-attached to the body-side coupling member 44. Nevertheless, the body-side mounting member 46 remains worn on the body to enable replacement devices 30 (or other ostomy appliances) to be fitted without having the change the body-side mounting member 46.

In a particularly preferred form described in more detail later, the cap 32 acts as a structural bracing member for bracing the second ostomy coupling 42 when the first ostomy coupling 40 is also fastened. Separating the cap 32 to release the first ostomy coupling also removes the structural bracing of the second coupling 42. Such an arrangement combines the first and second ostomy couplings 40 and 42 into a combined coupling arrangement instead of the couplings 40 and 42 operating independently. The combined arrangement is also useful to promote separation of the cap 32 from the mounting ring 36 (i.e., separation of the first ostomy coupling 40) before separation of the mounting ring 36 from the body-side coupling member 44 (i.e., before separation of the second ostomy coupling 42) in accordance with the intended and preferred order of use of the device 30.

The present invention envisages a wide variety of mechanical interference fasteners that are used to form a releasable fastening once, but which may become substantially inoperative after the first time the fastener is released. The act of releasing the fastener the first time may cause a fastener portion, or a support or brace therefore, to be deformed, broken or weaken, in order to render the fastener substantially inoperative thereafter.

Figure 9:
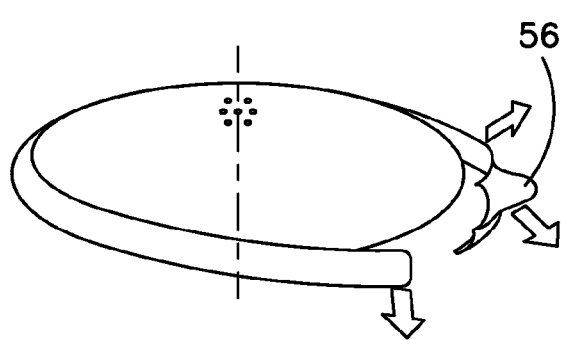
FIG. 9 is a schematic drawing of the mechanical fastener of FIG. 7 showing the tab being moved to achieve tearing.

Referring to FIGS. 7-10, a first example of a mechanical interference fastener generally comprises a retaining band 50 for retaining engagement between two ostomy coupling members 52 and 54. The retaining band 50 is a bracing band. In the configuration illustrated in FIGS. 7-9, the fastener may be applied to the first ostomy coupling 40 of the second embodiment. The band 50 may be comprised of heat shrinkable material (e.g., heat shrinkable plastics) that conforms to the opposing surfaces of the coupling members 52 and 54. The band 50 might, for example, be made of any oriented plastics, such as polyester, PET or polyolefin plastics, that shrink when heated from an initial shape 50' to the tensioned band shape 50. The band 50 may be die-cut from an extruded thin-wall tube of such material. The band 50 may be comprised of an exposed tab 56 and one or more lines of perforations 58 to promote tearing of the band 50 in a preferred direction when the fastener is to be released for the first time (FIG. 9). Tearing the band 50 open releases the hoop tension in the band 50, to permit the coupling parts to be separated. Without the strength of the band 50, the coupling parts are not refastenable in a secure manner for re-use.

To aid assembly during manufacture, the coupling members 52 and 54 may additionally comprise undercuts or latching features 60 which serve to hold the coupling members together weakly prior to the band 50 being fitted. Such latch/undercut features 60 may have a wide variety of coupling strengths depending on the requirements of the device. Typically, the band 50 would provide the majority of the retaining force. However, it may generally be desirable for the band 50 to provide between 5-95% of the total retaining force, depending on the application.

Figure 10:
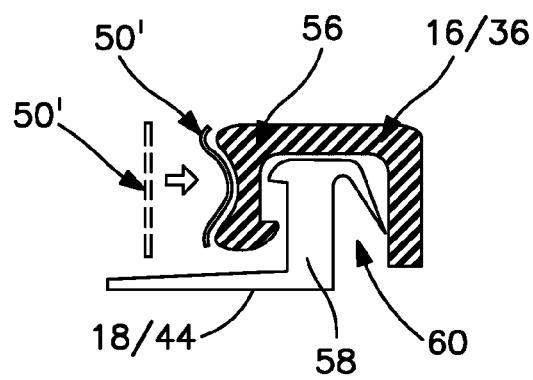
FIG. 10 is a schematic drawing showing a configuration of a retaining band on a coupling.
Figure 11:
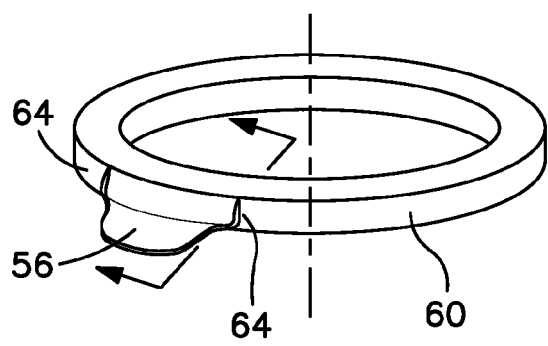
FIG. 11 is a schematic drawing of a second embodiment of mechanical fastener.
Figure 12:
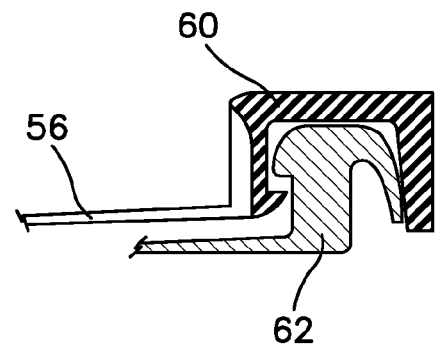
FIG. 12 is a schematic drawing showing the second embodiment of a mechanical fastener of FIG. 11 on a coupling.
Figure 13:
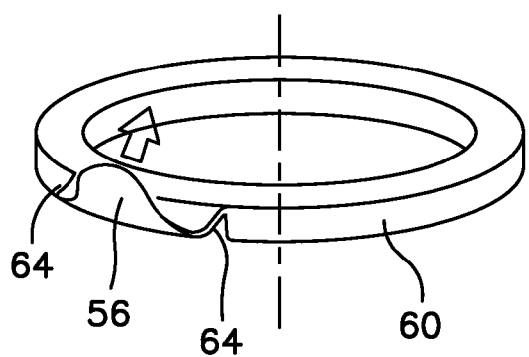
FIG. 13 is a schematic drawing of the second embodiment of a mechanical fastener of FIG. 11 with a tab for separation being lifted.
Figure 14:
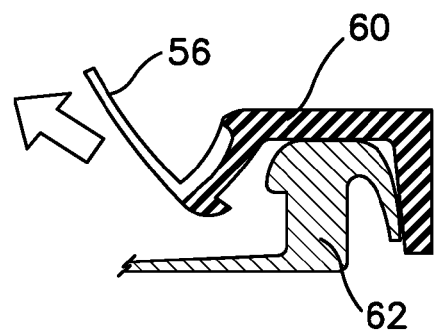
FIG. 14 is a schematic drawing of the second embodiment of a mechanical fastener of FIG. 11 on a coupling with a tab for separation being lifted.

FIG. 10 illustrates a configuration of the band 50 suitable for the ostomy coupling 14 of the first embodiment, or the second ostomy coupling 42 of the second embodiment. The band 50 encircles a fastener portion 56 of the non-body-side coupling member 16/36, in order to brace the fastener portion against outward flexing. The body-side coupling member 18/44 comprises a projection 58 that is received within a channel 60 of the non-body-side coupling member 16/36, as a tight, snap fit, when the two coupling members are pressed together for the first time. Thereafter, in order to separate the coupling members, it is necessary to remove the band 50 to thereby allow the fastener portion 56 of the non-body-side coupling member 16/36 to flex to release the snap engagement. With the band removed, the strength of the fastener portion 56 is significantly reduced, such that the fastener parts may not be re-placed in secure fastening engagement.

In the examples of FIGS. 7-10, the band 50 may be configured to be heat shrinkable from an initial form 50' into its retaining/bracing position. However, any means of inducing compressive hoop stress may be employed. The band 50 may alternatively be made from an elastic plastics film, preferably highly elastic, which could be stretched into its retaining/bracing position. The band 50 may be held in place by means of mating areas coated with pressure sensitive adhesive. Alternatively, the band may be configured as a length of material, the ends of which are overlap to form a continuous shape. The ends of the band 50 are may be locally bonded together using an applied adhesive. Alternatively, the majority or substantially entire inner surface of the band 50 may be coated with an adhesive that holds the band 50 in position on the coupling. Peeling the adhesively coated band 50 away from the coupling would allow irreversible separation of the coupling components. The band 50 may also be held in position by a localized thermal weld, holt melt adhesive, or a structural adhesive such as cyannoacrylate.

Referring to FIGS. 11-16 a second example of mechanical fastening comprises a fastener 60 comprising undercuts and/or latches for forming an interference fit with a complementary fastener 62. The interference fit has sufficient strength to hold the fastener parts together securely under all envisaged normal conditions of use. Separation of the fasteners 60 and 62 may be initiated by tearing or splitting the fastener 60. The fastener 60 may be split across its entire width, or alternatively only a portion of the fastener 60 may be split. For example, referring to FIG. 12 only a wall or portion that contains the latches is structurally compromised to allow separation of the fasteners 60 and 62. Splitting at least a portion of the wall would have two effects. Firstly, it would allow disengagement of the latches at the point at which the wall is split, to provide an initiation point for peeling the fasteners 60 and 62 apart. Secondly, it would allows the wall to flex outwardly on either side of the point at which the wall is split, thus extending the region of no, or only weak, engagement. FIGS. 11-14 illustrate the mechanical fastening applied to an ostomy coupling 14 of the first embodiment, or to the second ostomy coupling 42 of the second embodiment. FIGS. 15 and 16 illustrate the mechanical fastening applied to the first ostomy coupling 40 of the second embodiment.

The first fastener 60 may comprise one or more lines or regions 64 of weakness, to control tearing or splitting of the wall, for example by defining a preferential tearing path having a defined start and end. For example, the regions 64 of weakness are defined by partial depth or complete depth perforations in the wall material. Alternatively, the regions 64 of weakness may be defined by a gap or rebate in the wall material. The gap or rebate may, if desired, be covered, filled, bridged or over-molded, with a weaker material. For example, a thin film may be welded over the gap, or a weaker plastics may be added by an insert molding or multi-shot molding process.

Figure 17:
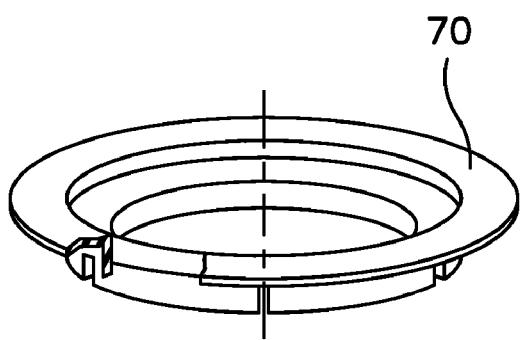
FIG. 17 is a schematic drawing showing a third embodiment of a mechanical fastener.
Figure 18:
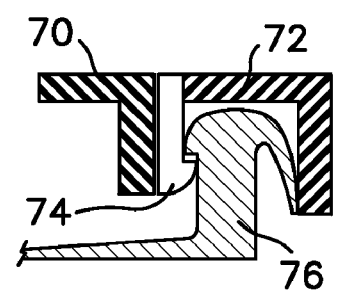
FIG. 18 is a schematic drawing of a third embodiment of a mechanical fastener of FIG. 17 in place on a coupling.

Referring to FIGS. 17-19, a third example of mechanical fastening comprises a relatively rigid outer bracing ring 70 that is configured to brace a wall of one fastener part 72 to hold latches 74 in fastening engagement with a complementary fastener part 76. The fastener parts 72 and 76 are configured to allow the fastener parts to be pressed into engagement as a snap-fit, whereafter the latches 74 resist separation of the fastener parts 72 and 76. The bracing ring 70 may be disengageable from its bracing position by sliding, or hinging, movement, as depicted in FIG. 19. Once the bracing effect has been removed, the latches 74 are free to flex outwardly, either naturally or in response to a separation force, to permit the fastener parts 72 and 76 to be separated. The bracing ring 70 could initially be retained in position by any suitable means, preferably by a mechanism that is broken irreversibly when the bracing ring 70 is displaced. For example, the bracing ring may be secured by adhesive, welding, or by integral molding, for example, multi-shot molding. Regions of bonding between the ring 70 and the fastener part 72 may function as weak points that are broken upon movement of the ring 70. The ring 70 and/or the fastener part 72 may additionally be configured to obstruct replacement of the ring 70 in its bracing position.

The example of FIGS. 17-19 illustrates in a form suitable as the ostomy coupling 14 of the first embodiment, or the second ostomy coupling 42 of the second embodiment. Alternatively, the example of FIGS. 17-19 could implement a combination of both the first and second ostomy couplings 40 and 42 of the second embodiment. For example, the bracing ring 70 may be implemented as part of the cap 32, the fastener part 72 may be implemented as the mounting ring 36 and the fastener part 77 may be implemented as the body-side coupling member 44.

Figure 21:
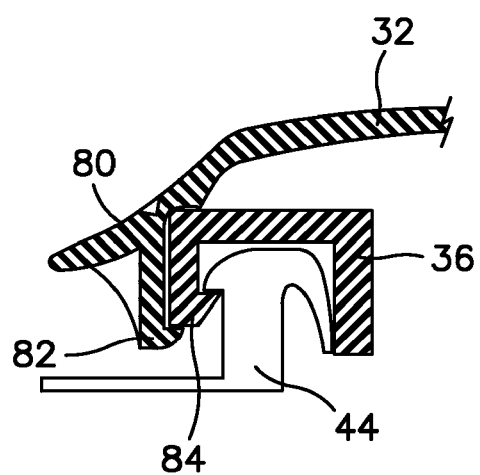
FIG. 21 is a schematic drawing of the fourth embodiment of the mechanical fastener of FIG. 20 in place on a coupling.
Figure 22:
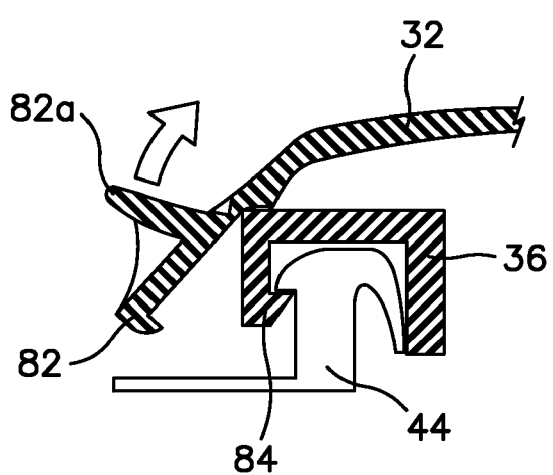
FIG. 22 is a schematic drawing of the fourth embodiment of the mechanical fastener of FIG. 20 being disengaged from a coupling.

FIGS. 20-22 illustrate a further example of fastener similar to FIGS. 17-19, but especially configured for implementing a combination of the first and second ostomy couplings 40 and 42 of the second embodiment. Referring to FIGS. 20-22, the cap 32 is configured with a skirt 80 that acts as a bracing ring around the mounting ring 36 and the body-side coupling member 44 when mutually assembled together. The skirt 80 includes one or more latches 82 that engage under the mounting ring 36 to retain the cap 32 on the mounting ring 36 (the first ostomy coupling). The mounting ring 36 includes one or more latches 84 that engage the body-side coupling member 44 to retain the mounting ring on the body-side coupling member 46 (the second ostomy coupling). The skirt 80 braces the mounting ring 36 to stiffen the entire assembly, and thereby securely retaining all of the cap 32, the mounting ring 36 and the body-side coupling member 44 in secure and tight mechanical fastening engagement.

The cap 32 includes one or more regions of weakness 86 to define a tear path for spitting the skirt 80 to remove the bracing effect when it is desired to separate the cap 32. The regions of weakness 86 define a flap portion 82a of the skirt 80 that is pivoted upwardly. Upon releasing the bracing effect of the skirt 80, the cap 32 is separated easily from the mounting ring 36. Releasing the bracing effect also enables the mounting ring 36 to be separated more easily from the body-side coupling member 44 in due course when it is desired to remove the device 30 therefrom. Once the skirt 80 has been split, the cap 32 may not be refastened securely to the mounting ring 36, as the skirt 80 will not provide any structural support.

Figure 23:
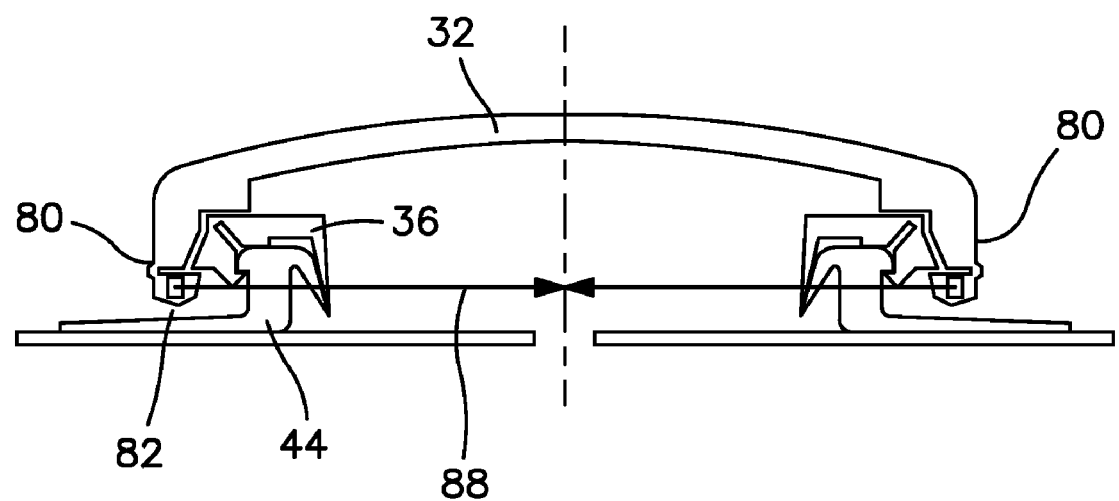
FIG. 23 is a schematic drawing showing a mechanical fastener in place on a joined body side coupling member and a cap.

FIG. 23 illustrates a modified form of the fastener example of FIGS. 20-22. Referring FIG. 23, the mounting ring 36 and/or the skirt fasteners 82 may be implemented as a living hinge. The cap 32 comprises a bracing band 88 to compress the skirt fasteners 82, and the mounting ring 32 into tight secure mechanical fastening engagement. The bracing band 88 may be interiorly mounted within the cap 32. The bracing band 88 may be implemented as a cable. The cable may be tensioned by means of a clasp, or over-centre buckle, a threaded turnbuckle or a ratchet mechanism. In use, the bracing band 88 is cut or deformed or enlarged either prior to, or by the action of, removing the cap 32. Such manipulation of the band 88 permanently removes the bracing effect of the skirt 80.

It may be appreciated that the examples of FIGS. 17-23 when applied to the second embodiment provides specific advantages in combining the first and second couplings 40 and 42 into a combined coupling arrangement. The combined arrangement is useful to promote separation of the cap 32 from the mounting ring 36 (i.e., separation of the first ostomy coupling 40) before separation of the mounting ring 36 from the body-side coupling member 44 (i.e., before separation of the second ostomy coupling 42) in accordance with the intended and preferred order of use of the device 30.

It will be appreciated that the foregoing description is merely illustrative of preferred forms of the invention, and that many modifications, are within the scope of the invention.

We claim:

1. An ostomy appliance for use by a person with a stomal orifice comprising:
    a. a body-side coupling member for attachment to the person around the stomal orifice, said body-side coupling member including a coupling; and
    b. a disposable ostomy member intended for single use, said disposable ostomy member including a cap with a releasable folded collection pouch therewithin, said collection pouch being secured to said cap and having an open end for receiving body waste from the stomal orifice, said cap including a cap coupling for coupling said cap to said body-side coupling, said cap coupling including a tearable channel wall, said channel wall forming an interference fit with said body-side coupling, said cap coupling further including an integral tab being moveable relative to said wall so as to tear said wall, said wall being adequately flexible upon tearing so as to weaken the coupling of said body-side coupling and cap coupling and permit peeling apart of said couplings, said ostomy member being unresecurable to said body-side coupling after tearing of said wall.

2. The ostomy appliance according to claim 1, tearing of said wall transforms the unitary disposable ostomy appliance from a first operation state to a second operation state.

3. The ostomy appliance according to claim 2, wherein the first operation state is a compact state, in which the appliance has a folded collection pouch and reduced collection volume for stomal waste.

4. The ostomy appliance according to claim 2, wherein the second operation state is an enlarged state, in which the appliance has an unfolded collection pouch and an enlarged collection volume for stomal waste.

\* \* \* \* \*